US00PP12897P2

(12) United States Plant Patent
van Rijn

(10) Patent No.: US PP12,897 P2
(45) Date of Patent: Aug. 27, 2002

(54) ANTHURIUM PLANT NAMED 'VR 110'

(75) Inventor: Leonardus W. B. M. van Rijn, Schipluiden (NL)

(73) Assignee: RijnPlant B.V., Schipluiden (NL)

( * ) Notice: Subject to any disclaimer, the term of this patent is extended or adjusted under 35 U.S.C. 154(b) by 18 days.

(21) Appl. No.: 09/837,570

(22) Filed: Apr. 18, 2001

(51) Int. Cl.[7] ..... A01H 5/00
(52) U.S. Cl. ..... Plt./367

(58) Field of Search ..... Plt./367

*Primary Examiner*—Bruce R. Campell
*Assistant Examiner*—Annette H. Para
(74) *Attorney, Agent, or Firm*—C. A. Whealy

(57) ABSTRACT

A distinct cultivar of Anthurium plant named 'VR 110', characterized by its upright and somewhat outwardly spreading plant habit; dark green leaves; dark pink-colored spathes with light yellow-colored spadices that are positioned upright and beyond the foliage on strong and erect scapes; and good inflorescence longevity.

2 Drawing Sheets

BACKGROUND OF THE INVENTION

The present invention relates to a new and distinct cultivar of Anthurium plant, botanically known as *Anthurium andreanum*, and hereinafter referred to by the name 'VR 110'.

The new Anthurium is a product of a planned breeding program conducted by the Inventor in Schipluiden, The Netherlands. The objective of the program is to create and develop new freely flowering Anthurium cultivars with strong roots, dark green leaves, attractive spathe color, and good inflorescence longevity.

The new Anthurium originated from a cross by the Inventor in 1996 of the Inventor's proprietary *Anthurium andreanum* selection code number 90-0026 as the female, or seed, parent with the Inventor's proprietary *Anthurium andreanum* selection code number 95-003 as the male, or pollen, parent. The cultivar VR 110 was discovered and selected by the Inventor as a plant within the progeny of the stated cross in a controlled environment in Schipluiden, The Netherlands in 1998.

Asexual propagation of the new cultivar by tissue culture in a laboratory in Belgium has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar VR 110. These characteristics in combination distinguish 'VR 110' as a new and distinct cultivar:

1. Upright and somewhat outwardly spreading plant habit.

2. Durable dark green leaves.

3. Dark pink-colored spathes with light yellow-colored spadices that are positioned upright and beyond the foliage on strong and erect scapes.

4. Freely flowering habit.

5. Good inflorescence longevity.

The new Anthurium can be compared to the female parent, the selection 90-0026. In side-by-side comparisons conducted in Schipluiden, The Netherlands, plants of the new Anthurium differ from plants of the selection 90-0026 in the following characteristics:

1. Plants of the new Anthurium are bushier than plants of the selection 90-0026.

2. Plants of the new Anthurium have smaller leaves than plants of the selection 90-0026.

3. Spathe color of plants of the new Anthuriums is lighter than spathe color of plants of the selection 90-0026.

The new Anthurium can be compared to the male parent, the selection 95-003. In side-by-side comparisons conducted in Schipluiden, The Netherlands, plants of the new Anthurium differ from plants of the selection 95-003 in the following characteristics:

1. Plants of the new Anthurium are bushier than plants of the selection 95-003.

2. Plants of the new Anthurium have more durable leaves than plants of the selection 95-003.

3. Spathe color of plants of the new Anthuriums is lighter than spathe color of plants of the selection 95-003.

The new Anthurium can also be compared to the cultivar Elisabeth, disclosed in U.S. Plant Pat. No. 9,704. In side-by-side comparisons conducted in Schipluiden, The Netherlands, plants of the new Anthurium differ from plants of the cultivar Elisabeth in the following characteristics:

1. Plants of the new Anthurium are bushier than plants of the cultivar Elisabeth.

2. Plants of the new Anthurium have smaller leaves than plants of the cultivar Elisabeth.

3. Plants of the new Anthurium have smaller spathes than plants of the cultivar Elisabeth.

4. Plants of the new Anthurium and the cultivar Elisabeth differ in spathe coloration.

BRIEF DESCRIPTION OF THE PHOTOGRAPHS

The accompanying colored photographs illustrate the overall appearance of the new Anthurium, showing the colors as true as it is reasonably possible to obtain in colored reproductions of this type. Colors in the photographs may differ slightly from the color values cited in the detailed botanical description which accurately describe the colors of the new Anthurium.

The photograph on the first sheet comprises a side perspective view of a typical potted plant of the cultivar VR 110 that was about three years old.

The photograph at the top of the second sheet comprises a close-up view of typical inflorescences of 'VR 110'.

The photograph at the bottom of the second sheet comprises a close-up view of a typical leaf of 'VR 110'.

DETAILED BOTANICAL DESCRIPTION

In the following description, color references are made to The Royal Horticultural Society Colour Chart except where general terms of ordinary dictionary significance are used. The following observations and measurements describe 3-year old plants grown in 19-cm containers in Schipluiden, The Netherlands, in a glass greenhouse with an average day temperature of 25° C. and an average night temperature of 19° C.

Botanical classification: *Anthurium andreanum* cultivar VR 110.

Parentage:

*Female parent.*—Inventor's proprietary *Anthurium andreanum* selection code number 90-0026, not patented.

*Male parent.*—Inventor's proprietary *Anthurium andreanum* selection code number 95-003, not patented.

Propagation:

*Method.*—By tissue culture.

*Time to develop roots on a tissue-cultured cutting.*—About 70 or 84 days at 24° C. or 21° C., respectively.

*Root description.*—Strong fleshy roots.

Plant description:

*Plant shape.*—Upright and somewhat outwardly spreading, inverted triangle, symmetrical.

*Growth habit.*—Freely clumping, bushy and dense. Appropriate for 17 to 35-cm containers. Vigorous.

*Plant height.*—About 70 to 95 cm.

*Crop time.*—About 10 months are usually required from planting of young plants to finished plants in a 17-cm container.

*Foliage description.*—Quantity per plant: About 80. Length: About 20 to 30 cm. Width: About 12 to 19 cm. Shape: Cordate. Apex: Apiculate. Base: Auriculate; lobes not overlapping. Margin: Entire. Texture: Smooth, glabrous, leathery. Venation pattern: Pinnate. Color: Young leaves, upper surface: Between 137A and 143A. Young leaves, lower surface: 147C. Mature leaves, upper surface: 137A; venation, 145A. Mature leaves, lower surface: 143C to 143D; venation, 145B. Petiole: Length: About 20 to 45 cm. Color: 144A. Geniculum length: About 2 to 3 cm. Geniculum color: 144A.

Inflorescence description:

*Inflorescence arrangement.*—Spathes with spadices held beyond the foliage. Flowering structures arise from leaf axils. Freely and continuous flowering year-round; typically more than 25 inflorescences per plant.

*Inflorescence longevity.*—Inflorescences last about six weeks under winter conditions and about three months under summer conditions; persistent.

*Spathe.*—Length: About 12 to 17 cm. Width: About 13 to 18 cm. Shape: Cordate. Apex: Apiculate to mucronulate. Base: Auriculate; lobes not overlapping. Margin: Entire. Texture: Leathery, glabrous, some blistering. Color: When opening: Apex and center, 47B; towards base, 143B; glossy. Opened, front surface: 47B; glossy. Opened, back surface: 51B; glossy.

*Spadix.*—Length: About 5 to 7 cm. Diameter: About 1 cm. Shape: Columnar. Cross section: Rounded. Longitudinal axis: Erect. Color: Immature: 144C to 150A. Mature: 11B.

*Flowers.*—Quantity per spadix: Numerous, about 200. Shape: Rounded. Diameter: About 1 mm, maximum.

*Reproductive organs.*—Androecium: Pollen color: 159B. Gynoecium: Stigma shape: Ovoid.

*Scape.*—Length: About 40 to 70 cm. Aspect: Strong and erect. Color: 144A to 146B.

*Seed.*—Seed development on plants of the new Anthurium has not been observed.

Disease/pest resistance: Under commercial conditions, plants of the new Anthurium have not been observed to be resistant to pathogens or pests common to Anthurium.

It is claimed:

1. A new and distinct cultivar of Anthurium plant named 'VR 110', as illustrated and described.

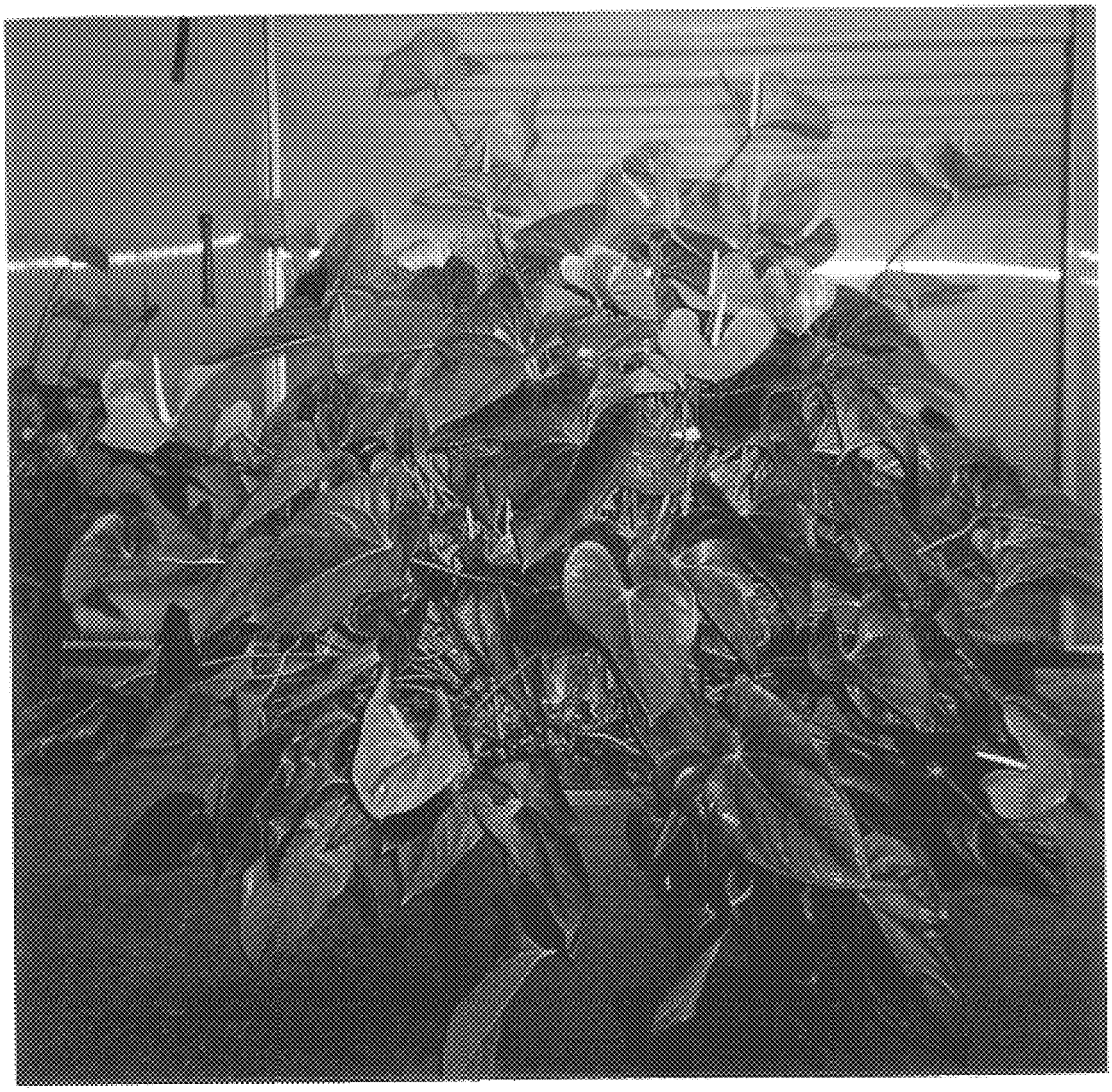

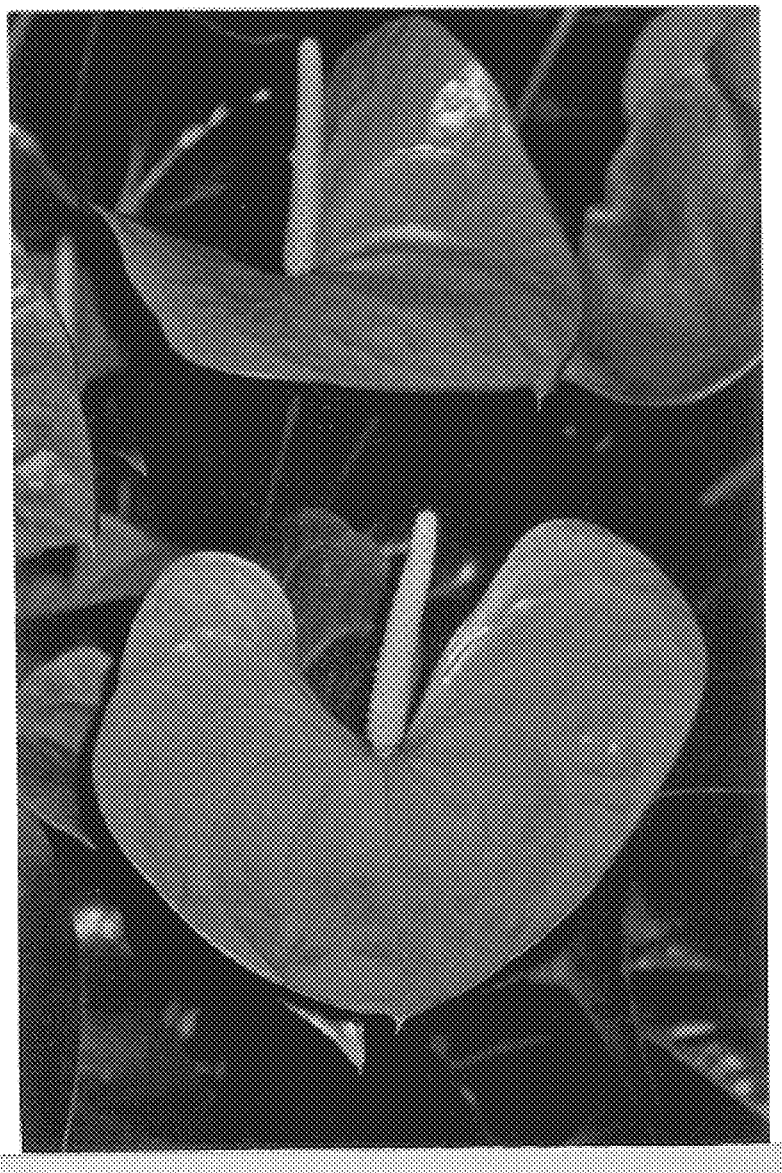
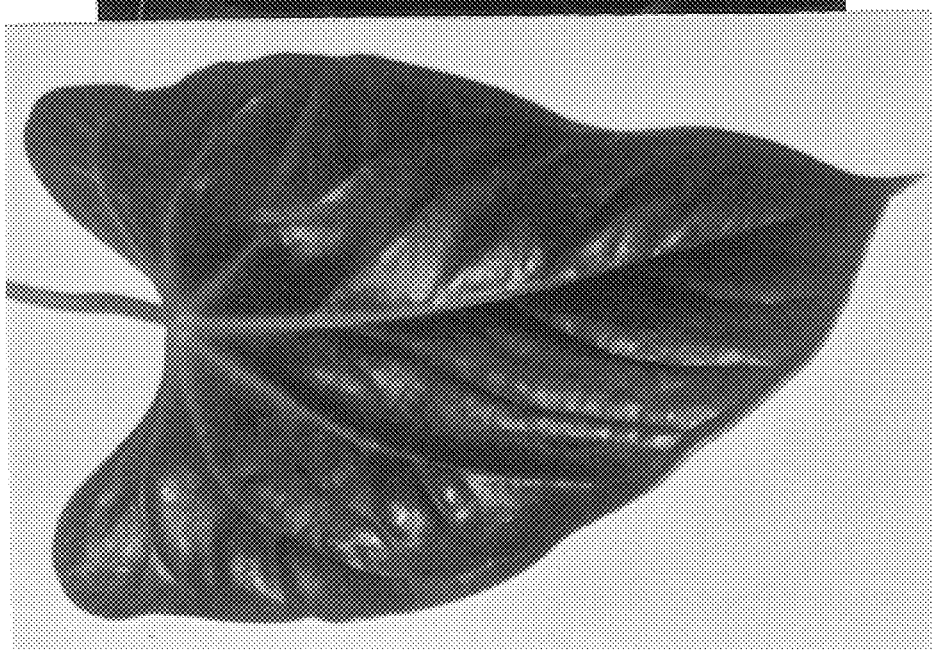

* * * * *